United States Patent [19]

Tobin et al.

[11] 4,224,449
[45] Sep. 23, 1980

[54] BIURET DERIVATIVES OF 3-TRIHALOMETHYL-1,2,4-THIADIAZOLES

[75] Inventors: John H. Tobin, Winsted; Walter A. Gay, Cheshire; Lawrence E. Katz, Orange, all of Conn.

[73] Assignee: Olin Corporation, New Haven, Conn.

[21] Appl. No.: 64,923

[22] Filed: Aug. 8, 1979

[51] Int. Cl.³ .................... A01N 47/36; C07D 285/08
[52] U.S. Cl. ........................................ 548/128; 71/73; 71/90
[58] Field of Search .................. 548/128; 71/90, 73

[56] References Cited

U.S. PATENT DOCUMENTS

| | | | |
|---|---|---|---|
| 3,260,588 | 7/1966 | Schroeder | 71/90 |
| 3,260,725 | 7/1966 | Schroeder | 548/128 |
| 3,324,141 | 6/1967 | Bernstein | 548/128 |
| 3,573,317 | 3/1971 | Smith | 548/128 |
| 3,629,275 | 12/1971 | Metzger et al. | 548/128 |
| 3,651,075 | 3/1972 | Miller | 548/128 |
| 3,673,203 | 6/1972 | Miller | 548/128 |
| 3,686,198 | 8/1972 | Metzger et al. | 548/128 |
| 3,720,684 | 3/1973 | Krenzer et al. | 548/128 |
| 3,764,685 | 10/1973 | Krenzer et al. | 548/128 |
| 3,770,749 | 11/1973 | Phillips | 260/294.8 D |
| 3,822,280 | 7/1974 | Moser et al. | 71/90 |
| 3,873,299 | 3/1975 | Metzger et al. | 548/128 |
| 3,884,929 | 5/1975 | Smith | 548/128 |
| 3,917,478 | 11/1975 | Moser et al. | 548/128 |
| 4,107,377 | 8/1978 | Tobin | 548/128 |

*Primary Examiner*—Alton D. Rollins
*Attorney, Agent, or Firm*—William A. Simons; Thomas P. O'Day

[57] ABSTRACT

Disclosed are selected biuret derivatives of 3-trihalomethyl-1,2,4-thiadiazole compounds of the formula:

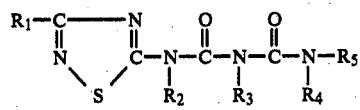

wherein $R_1$ is a $CCl_3$ or $CF_3$ group; $R_2$ and $R_3$, separately, are either hydrogen or a lower alkyl group of 1 to 4 carbon atoms or an aryl group having 6 to 8 carbon atoms; and $R_4$ and $R_5$ are either hydrogen or a lower alkyl group of 1 to 4 carbon atoms or an aryl group having 6 to 8 carbon atoms or an acyl group having 1 to 8 carbon atoms, with the proviso that either $R_4$ or $R_5$, or both, must be a hydrogen.

10 Claims, No Drawings

BIURET DERIVATIVES OF 3-TRIHALOMETHYL-1,2,4-THIADIAZOLES

BACKGROUND OF THE INVENTION

1. Field of the Invention

This invention relates to selected biuret derivatives of 3-trihalomethyl-1,2,4-thiadiazole compounds and their use as herbicides.

2. Description of the Prior Art

Various 3,5-substituted-1,2,4-thiadiazole compounds have been known to possess different types of pesticidal activity such as fungicidal, herbicidal, insecticidal and the like. For example, U.S. Pat. No. 3,673,203, which issued to A. H. Miller on June 27, 1972, discloses that selected 1,2,4-thiadiazole ureas may be used as herbicides.

Furthermore, U.S. Pat. Nos. 3,686,198 and 3,873,299, both of which issued to C. Metzger, et al on Aug. 22, 1972 and Mar. 25, 1975, respectively, also disclose the use of other 1,2,4-thiadiazole ureas as herbicides. Still further, U.S. Pat. Nos. 3,822,280 and 3,917,478, both of which issued to H. Moser and C. Vogel on July 2, 1974 and Nov. 4, 1975, respectively, disclose the use of still other 1,2,4-thiadiazole ureas as herbicides. However, none of these artisans recognized that selected biuret derivatives of 1,2,4-thiadiazoles may also possess herbicidal properties.

BRIEF SUMMARY OF THE INVENTION

Accordingly, the present invention is directed to, as compositions of matter, selected biuret derivatives of 3-trihalomethyl-1,2,4-thiadiazole compounds of the formula:

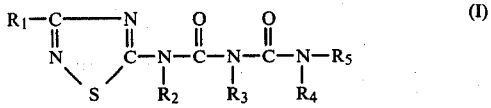

(I)

wherein $R_1$ is a $CCl_3$ or $CF_3$ group; $R_2$ and $R_3$, separately, are either hydrogen or a lower alkyl group of 1 to 4 carbon atoms or an aryl group having 6 to 8 carbon atoms; and $R_4$ and $R_5$ are either hydrogen or a lower alkyl group of 1 to 4 carbon atoms or an aryl group having 6 to 8 carbon atoms or an acyl group having 1 to 8 carbon atoms, with the proviso that either $R_4$ or $R_5$, or both, must be a hydrogen.

DETAILED DESCRIPTION

The 5-biuret derivative compounds of the present invention may be prepared by reacting the corresponding 5-amino-3-trihalomethyl-1,2,4-thiadiazole or 5-ureido-3-trihalomethyl-1,2,4-thiadiazole with the desired isocyanate preferably in the presence of a suitable solvent such as benzene or the like. This general reaction is illustrated in Equations (A) and (B), below. In Equation (A) 1 mole of 5-amino-3-trichloromethyl-1,2,4-thiadiazole is reacted with 2 moles of methyl isocyanate to prepare 1,3-dimethyl-5-(3-trichloromethyl-1,2,4-thiadiazol-5-yl)biuret:

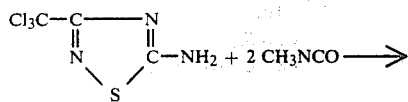

(A)

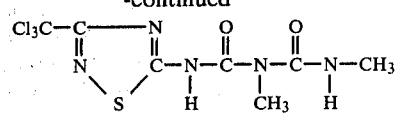

In Equation (B), 1-methyl-3-(3-trichloromethyl-1,2,4-thiadiazol-5-yl)urea is reacted with benzoyl isocyanate to prepare 1-benzoyl-3-methyl-5-(3-trichloromethyl-1,2,4-thiadiazol-5-yl)biuret:

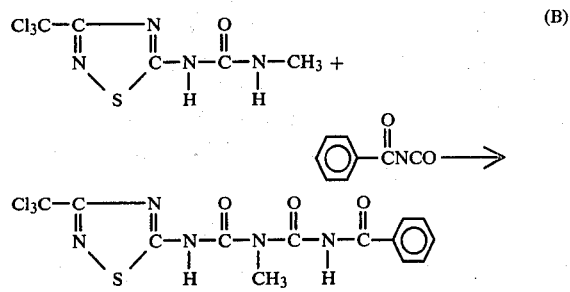

(B)

Suitable 5-amino substituted-3-trihalomethyl-1,2,4-thiadiazole reactants include 5-amino-3-trichloromethyl-1,2,4-thiadiazole, 5-methylamino-3-trichloromethyl-1,2,4-thiadiazole and 5-amino-3-trifluoromethyl-1,2,4-thiadiazole. 5-Amino-3-trichloromethyl and 5-methylamino-3-trichloromethyl-1,2,4-thiadiazole are both described in U.S. Pat. Nos. 3,260,588 and 3,260,725, both of which issued to H. A. Schroeder on July 12, 1966, and are made by reacting 5-chloro-3-trichloromethyl-1,2,4-thiadiazole with ammonia or methylamine, respectively. 5-Amino-3-trifluoromethyl-1,2,4-thiadiazole is described in U.S. Pat. No. 3,917,478, which issued to Moser et al on Nov. 4, 1975, and is prepared by (1) the side-chain fluorination of 5-chloro-3-trichloromethyl-1,2,4-thiadiazole with a Swarts' fluorination mixture consisting of antimony trifluoride, antimony trichloride and chlorine, followed by (2) ammoniation of 5-chloro-3-trifluoromethyl-1,2,4-thiadiazole.

Suitable 5-ureido-3-trihalomethyl-1,2,4-thiadiazole reactants include 1-methyl-3-(3-trichloromethyl-1,2,4-thiadiazol-5-yl)urea. This compound is described in U.S. Pat. No. 3,822,280 which issued to H. M. Basel and C. Vogel on July 2, 1977 and is made by reacting 5-amino-3-trichloromethyl-1,2,4-thiadiazole with methyl isocyanate.

Suitable isocyanate reactants include typical alkyl, aryl and acyl isocyanates such as methyl isocyanate, phenyl isocyanate, and benzoyl isocyanate, respectively. These reactants are made from amines and phosgene according to many conventional processes.

Any conventional reaction conditions designed to produce biurets may be employed in the synthesis of the present compounds and the present invention is not intended to be limited to any particular reaction conditions. Advantageously and preferably, the reactions are performed with a molar excess of the desired isocyanate reactant (e.g., from about 0.01 to about 10 moles excess) and in the presence of a suitable inert solvent. An aromatic hydrocarbon, such as benzene or xylene, is a preferred solvent, but other inert solvents, such as dimethylacetamide, may be used. The reaction temperature and time will both depend upon many factors, including the specific reactants used. In most situations, reaction temperatures from about 90° C. to about 200°

C. and reaction times from 0.1 hour to about 30 hours may be preferred. The desired product may be recovered from the reaction mixture by any conventional means, for example, extraction, trituration, and the like. Finally, it should be noted that while the reaction illustrated by Equations (A) and (B) are preferred methods of preparing the compounds of the present invention, other synthesis methods may also be employed.

In accordance with the present invention, it has been found that compounds of Formula (I) above, may be used for defoliation or for desiccation of the green parts of plants especially when applied as a post-emergent herbicide. They are, in particular, suitable singly, or in mixtures thereof, for the control of weeds. As contemplated herein, the term "weeds" is meant to include not only weeds in the narrow sense, but also in the broad sense, whereby to cover all plants and vegetation considered undesirable for the particular purposes in question. Whether the active compounds according to the present invention act as total or selective herbicides depends essentially on the amount applied, as the artisan will appreciate.

Specifically, in practicing the process of the present invention, undesirable plant and vegetation are contacted with a herbicidally effective amount of the above-mentioned compounds. It is to be understood that the term "herbicidally effective amount" as used in the the specification and claims herein is intended to include any amount that will kill or control said undesirable plants and vegetation when either employed by itself (i.e., in full concentration) or in sufficient concentration with a carrier or other substance. Of course, this amount may be constantly changing because of the possible variations in many parameters. Some of these may include: the number and type of plants to be controlled or killed; the type of loci or media to which the present compounds can be applied (e.g., weeds within crop areas, fence lines); degree of effectiveness required; and type of carrier, if any. The step of contacting may be accomplished by applying the present active compounds to the undesirable plants themselves or to the immediate locus or ground surrounding said plants. For most situations, the application of the compounds of the present invention in amounts from about 0.1 pounds per acre to about 10 pounds per acre will be sufficient for selective or total herbicidal effect.

The above-mentioned compounds of the present invention may be formulated and applied by any conventional methods that include using the compounds alone or with a carrier or other substances which may enhance the effectiveness of the chemical or facilitate handling. Moreover, the activity of the present compounds may be broadened by the addition thereto of other known biocides such as fungicides, other herbicides, insecticides and the like.

Specific methods of formulating and applying these active compounds include applying them in the form of dusts, dust or emulsion concentrates, wettable powders, and concentrates, granulates, dispersions, sprays, solutions and the like.

The dusts and dust concentrates are usually prepared by simply grinding together the active compounds of the present invention with a finely divided inert diluent such as walnut flour, diatomaceous earth, fullers earth, attaclay, talc or kaolin. Dusts generally contain from about 1% to about 15% by weight of active compound and dust concentrates usually contain from about 16% to about 75% by weight active compound. In practice, dust concentrates are usually admixed with more inert diluent at the site of use to form dusts before being applied to undesirable plant foliage.

Wettable powders are generally prepared in the same manner as dust concentrates, but usually about 1% to 10% by weight of a dispersing agent, for example, an alkali metal lignosulfonate and about 1% to 10% of a surfactant, such as a non-ionic surfactant, are incorporated in the formulation. For most applications, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray application.

It is possible to formulate granulates whereby these active compounds are dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, one of the above-mentioned active compounds, or more than one active compound, is normally dissolved in a suitable organic solvent, solvent mixtures or water. As organic solvents, it is possible to use any suitable aliphatic and aromatic hydrocarbon or their derivatives. It is preferred that the solvent be odorless and, moreover, be inert to the active compound.

It should be clearly understood that such herbicide formulations, the ingredients which may make up such formulations other than the active compounds and the dosages, and means of applying these formulations may include all known and conventional substances, amounts and means, respectively, that are suitable for obtaining the desired herbicidal result. Therefore, such process parameters are not critical to the present invention.

The following examples further illustrate the present invention. All parts and percentages employed therein are by weight unless otherwise indicated.

EXAMPLE I 1,3-Dimethyl-5-(3-Trichloromethyl-1,2,4-thiadiazol-5-yl)biuret

A glass pressure vessel was charged with 27.5 grams (0.13 mole) 5-amino-3-trichloromethyl-1,2,4-thiadiazole, 17.9 grams (0.31 mole) methyl isocyanate, and 250 milliliters benzene. A magnetic stirring bar was added and the vessel sealed. The stirred reaction mixture was heated at 145° C. for 1.5 hours and then allowed to cool to room temperature where a urea by-product precipitates. The by-product was removed by filtration and the filtrate concentrated in vacuo to leave 27.2 grams (65% yield) of product. Recrystallization from methanol gave an analytically pure sample; m.p. 94° C.

Analysis—Calculated for $C_7H_8Cl_3N_5O_2S$: C, 25.82%; H, 2.42%: Cl, 31.95%; N, 21.06%; S, 9.95%. Found: C, 25.67%; H, 2.39%; Cl, 31.98%; N, 20.88%; S, 9.29%.

EXAMPLE II

1,3-Diphenyl-5-(3-Trichloromethyl-1,2,4-thiadiazol-5-yl)biuret

A glass pressure vessel was charged with 5.5 grams (0.03 mole) 5-amino-3-trichloromethyl-1,2,4-thiadiazole, 7.4 grams (0.06 mole) phenyl isocyanate and 50 milliliters benzene. A magnetic stirring bar was added and the vessel sealed. The stirred reaction mixture was heated at 145° C. for 1.5 hours and then allowed to cool to room temperature where a urea by-product precipitates. The by-product was removed by filtration and the filtrate concentrated in vacuo to leave 9.0 grams of crude product. Trituration with cold methanol gave 2.8 grams (24% yield) of pure product; m.p. 170° C.

Analysis—Calculated for $C_{17}H_{12}Cl_3N_5O_2S$: C, 44.70%; H, 2.65%; Cl, 23.29%; N, 15.33%; S, 7.02%. Found: C, 44.47%; H, 2.76%; Cl, 23.08%; N, 15.53%; S, 7.05%.

EXAMPLE III

1-Benzoyl-3-methyl-5-(3-trichloromethyl-1,2,4-thiadiazol-5-yl)biuret

A glass pressure vessel was charged with 5.5 grams (0.02 mole) 1-methyl-3-(3-trichloromethyl-1,2,4-thiadiazol-5-yl)urea, 3.2 grams (0.02 mole) benzoyl isocyanate and 50 milliliters benzene. A magnetic stirring bar was added and the vessel sealed. The stirred reaction mixture was heated at 145° C. for 1.5 hours and then allowed to cool to room temperature where 4.5 grams of starting urea precipitates. The urea was removed by filtration and the filtrate concentrated in vacuo to leave 3.0 grams of residue. Extraction of the residue with hot cyclohexane, followed by cooling the extract yielded 0.2 grams (11% selectivity) of pure product; m.p. 70° C.

Analysis—Calculated for $C_{13}H_{10}Cl_3N_5SO_3$ C, 36.94%; H, 2.38%; Cl, 25.17%; N, 16.57%; S, 7.59% Found: C, 37.26%; H, 2.18%; Cl, 25.36%; N, 16.22%; S, 7.21%

EXAMPLE IV

The active material made in Example I was tested for activity as an effective herbicide by the following method.

A uniform aqueous dispersion of the chemical was made by dissolving the chemical in a solution of acetone containing a non-ionic surfactant in a concentration of 500 ppm. The resulting solution was diluted with water (1:9) to obtain a mixture of 10% acetone, 50 ppm surfactant, 0.208% by weight test candidate made in Example I, and the balance water; 50 milliliters of this solution applied to a flat of 144 square inches corresponds to 10 lb/acre. If further dilutions were required for testing at lower concentrations, water was added to this stock solution and the surfactant maintained at 50 ppm.

The aqueous solutions containing each chemical were applied to flats seeded with representative monocotyledonous and dicotyledonous plants. The test chemical was applied to one such flat immediately after it was seeded (pre-emergence screening) and to the other flat after the first true plant leaves had developed (post-emergence screening). Response was rated 12 to 21 days after treatment on a scale of 0 to 10, where 0 represents no injury and 10 represents complete kill.

The crops and weeds used for the determination of activity were: Foxtail Millet (*Setaria italica*), Japanese Millet (*Echinochloa crusgalli*), Crabgrass (*Digitaria sanguinalis*), Morning Glory (*Ipomoea purpurea*), Mustard (*Brassica nigra*), Pigweed (*Amaranthus retroflexus*), Sesbania (*Susbania exaltata*), Velvet Leaf (*Abutilon theophrasti*), Soybean (*Glycine max*), Cotton (*Gossypium hirsutum*), Cocklebur (*Xanthium strumirium L.* var *canadense*), Jimsonweed (*Datura Stramanium*), Bindweed (*Convolvulus arvensis L.*), Curly Doc (*Rumex crispus L.*), and Purslane (*Portulaca oleracea L.*).

The following Table illustrates the herbicidal activity for the compound made in Example I as determined by the above-stated herbicidal screening method.

| | HERBICIDAL ACTIVITY | | | | |
|---|---|---|---|---|---|
| | PRE-EMERGENCE | POST-EMERGENCE | | | |
| | 10 lb/Acre | 10 lb/Acre | 2.5 lb/Acre | 1.25 lb/Acre | 0.63 lb/Acre |
| Soybean | 1 | 8 | 4 | 3 | 2 |
| Cotton | * | 2 | 3 | 1 | 1 |
| Foxtail Millet | 2 | 10 | 9 | 9 | 10 |
| Japanese Millet | 2 | 7 | 5 | 4 | 3 |
| Crabgrass | * | 8 | 7 | 8 | 6 |
| Morning Glory | 8 | 10 | 10 | 10 | 4 |
| Mustard | 3 | 10 | 10 | 10 | 6 |
| Sesbania | * | 7 | 7 | 6 | 5 |
| Pigweed | 1 | 9 | 3 | 1 | 3 |
| Cocklebur | * | 0 | 0 | 1 | 0 |
| Jimsonweed | * | 1 | * | 1 | 6 |
| Velvet Leaf | * | 10 | 10 | 5 | 2 |
| Bindweed | * | 1 | * | 1 | 0 |
| Curley Doc | * | 3 | * | 3 | 1 |
| Purslane | * | 1 | * | 1 | 4 |

*not tested

What is claimed is:

1. A compound of the formula

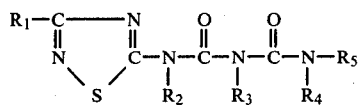

wherein $R_1$ is a $CCl_3$ or $CF_3$ group; $R_2$ and $R_3$, separately, are a hydrogen or a lower alkyl group of 1 to 4 carbon atoms or a phenyl group; and $R_4$ and $R_5$ are either hydrogen or a lower alkyl group of 1 to 4 carbon atoms or a phenyl group or a benzoyl group, with the proviso that either $R_4$ or $R_5$ or both, must be a hydrogen.

2. The compound of claim 1 wherein $R_1$ is $CCl_3$.

3. The compound of claim 1 wherein $R_2$ is hydrogen.

4. The compound of claim 3 wherein $R_4$ and $R_5$ are, subject to said proviso, selected from the group consisting of hydrogen and lower alkyl groups having 1 to 4 carbon atoms.

5. The compound of claim 4 having the formula:

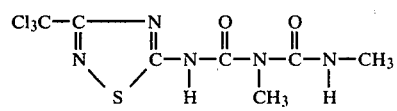

6. The compound of claim 3 having the formula:

7. The compound of claim 3 having the formula:
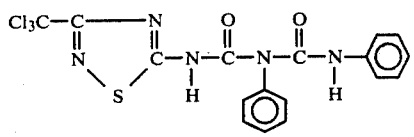
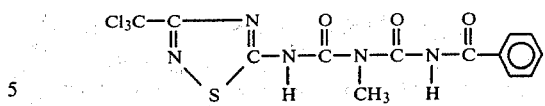
8. The compound of claim 3 wherein $R_1$ is $CCl_3$.
9. The compound of claim 8 wherein $R_3$ is a lower alkyl compound having 1 to 4 carbon atoms.
10. The compound of claim 8 wherein $R_3$ is a phenyl group.
* * * * *